US008198496B2

(12) United States Patent
Helton et al.

(10) Patent No.: US 8,198,496 B2
(45) Date of Patent: Jun. 12, 2012

(54) PROCESS OF MAKING ALKYLAROMATICS USING EMM-13

(75) Inventors: Terry E. Helton, Bethlehem, PA (US); Matthew J. Vincent, Baytown, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 12/999,484

(22) PCT Filed: Jul. 15, 2009

(86) PCT No.: PCT/US2009/050724
§ 371 (c)(1), (2), (4) Date: Jan. 31, 2011

(87) PCT Pub. No.: WO2010/014404
PCT Pub. Date: Feb. 4, 2010

(65) Prior Publication Data
US 2011/0144401 A1     Jun. 16, 2011

Related U.S. Application Data (60) Provisional application No. 61/084,171, filed on Jul. 28, 2008.

(30) Foreign Application Priority Data
May 25, 2009   (EP) .................................... 08165754

(51) Int. Cl.
*C07C 2/66* (2006.01)
(52) U.S. Cl. ...................................................... 585/467
(58) Field of Classification Search .................... 585/467
See application file for complete search history.

(56) References Cited

U.S. PATENT DOCUMENTS

| | | |
|---|---|---|
| 3,751,504 A | 8/1973 | Keown et al. |
| 4,016,218 A | 4/1977 | Haag et al. |
| 4,439,409 A | 3/1984 | Puppe et al. |
| 4,547,605 A | 10/1985 | Kresge et al. |
| 4,826,667 A | 5/1989 | Zones et al. |
| 4,891,458 A | 1/1990 | Innes et al. |
| 4,954,325 A | 9/1990 | Rubin et al. |
| 4,954,663 A | 9/1990 | Marler et al. |
| 4,956,514 A | 9/1990 | Chu |
| 4,962,239 A | 10/1990 | Bell et al. |
| 4,962,250 A | 10/1990 | Dessau et al. |
| 4,962,256 A | 10/1990 | Le et al. |
| 4,962,257 A | 10/1990 | Absil et al. |
| 4,968,402 A | 11/1990 | Kirker et al. |
| 4,973,784 A | 11/1990 | Han et al. |
| 4,982,033 A | 1/1991 | Chu et al. |
| 4,982,040 A | 1/1991 | Angevine et al. |
| 4,983,276 A | 1/1991 | Absil et al. |
| 4,986,894 A | 1/1991 | Keville et al. |
| 4,992,606 A | 2/1991 | Kushnerick et al. |
| 4,992,611 A | 2/1991 | Morrison |
| 4,992,615 A | 2/1991 | Huss, Jr. et al. |
| 5,000,839 A | 3/1991 | Kirker et al. |
| 5,001,283 A | 3/1991 | Altman et al. |
| 5,001,295 A | 3/1991 | Angevine et al. |
| 5,001,296 A | 3/1991 | Howley et al. |
| 5,012,033 A | 4/1991 | Child et al. |
| 5,013,422 A | 5/1991 | Absil et al. |
| 5,019,664 A | 5/1991 | Del Rossi et al. |
| 5,019,665 A | 5/1991 | Partridge et al. |
| 5,019,670 A | 5/1991 | Le et al. |
| 5,236,575 A | 8/1993 | Bennett et al. |
| 5,250,277 A | 10/1993 | Kresge et al. |
| 5,334,795 A | 8/1994 | Chu et al. |
| 5,362,697 A | 11/1994 | Fung et al. |
| 5,557,024 A | 9/1996 | Cheng et al. |
| 6,077,498 A | 6/2000 | Diaz Cabanas et al. |
| 6,936,744 B1 | 8/2005 | Cheng et al. |
| 6,984,764 B1 | 1/2006 | Roth et al. |
| 2004/0092757 A1 | 5/2004 | Oguchi et al. |
| 2005/0158238 A1 | 7/2005 | Tatsumi et al. |
| 2008/0027259 A1 | 1/2008 | Roth et al. |
| 2008/0045768 A1 | 2/2008 | Roth et al. |

FOREIGN PATENT DOCUMENTS

| | | |
|---|---|---|
| EP | 0 293 032 | 11/1988 |
| WO | 97/17290 | 5/1997 |
| WO | 2005/118476 | 12/2005 |
| WO | WO 2006/015824 | 2/2006 |
| WO | WO 2006/015825 | 2/2006 |
| WO | WO 2006/015826 | 2/2006 |

OTHER PUBLICATIONS

C. Baerlocher et al., "*Charge Flipping Combined With Histogram Matching to Solve Complex Crystal Structures From Powder Diffraction Data*", Z. Kristallogr., 2007, vol. 222, pp. 47-53.
W. Fan et al., "*Synthesis and Catalytic Properties of a New Titanosilicate Molecular Sieve With the Structure Analogous to MWW-Type Lamellar Precursor*", Journal of Catalyst, 2006, vol. 243, pp. 183-191.
C. Gilmore et al., "*A Multisolution Metohd of Phase Determination by Combined Maximization of Entropy and Likelihood. II. Application to Small Molecules*", Acta Cryst., 1990, A46, pp. 297-308.
C. Gilmore et al., "*A Multisolution Method of Phase Determination by Combined Maximization of Entropy and Likelihood. VI. The Use of Error-Correcting Codes as a Source of Phase Permutation and Their Application to the Phase Problem in Powder, Electron and Macromolecular Crystallography*", Acta Cryst., 1999, A55, pp. 70-83.
C. Gilmore et al., "*Applications of the Maximum Entropy Method to Powder Diffraction and Electron Crystallography*", Proc. R. Soc., London, 1993, vol. 442, pp. 97-111.

(Continued)

*Primary Examiner* — Thuan Dinh Dang
(74) *Attorney, Agent, or Firm* — Darryl M. Tyus (57) ABSTRACT

This disclosure relates to a process for manufacturing a mono-alkylaromatic aromatic compound, said process comprising contacting a feedstock comprising an alkylatable aromatic compound and an alkylating agent under alkylation reaction conditions with a catalyst comprising EMM-13, wherein said EMM-13 is a molecular sieve comprising a framework of tetrahedral atoms bridged by oxygen atoms, the tetrahedral atom framework being defined by a unit cell with atomic coordinates in nanometers shown in Table 3.

18 Claims, 1 Drawing Sheet

OTHER PUBLICATIONS

S. Hovmoller et al., "*CRISP: Crystallographic Image Processing on a Personal Computer*", Ultramicroscopy, 1992, vol. 41, pp. 121-135.

S. Kim et al., "*Structural Evolution of B-MCM-36 and B-ITQ-2 From B-MCM-22*", Bull Korean Chem. Soc., 2006, vol. 27, No. 10, pp. 1693-1696.

S. Lawton et al., "*Zeolite MCM-49: A Three-Dimensional MCM-22 Analogue Synthesized by In Situ Crystallization*", J. Phys. Chem., 1996, vol. 100, No. 9, pp. 3788-3798.

S. Maheshwari et al., "*Layer Structure Preservation During Swelling, Pillaring, and Exfoliation of a Zeolite Precursor*", J. Am. Chem. Soc., 2008, vol. 130, No. 4, pp. 1507-1516.

J. Ruan et al., "*Structure Elucidation of the Highly Active Titanosilicate Catalyst Ti-YNU-1*", Angew. Chem. Int. Ed., 2005, vol. 44, pp. 6719-6723.

R. Vincent et al., "*Double Conical Beam-Rocking System for Measurement of Integrated Electron Diffraction Intensities*", Ultramicroscopy, 1994, vol. 53, pp. 271-282.

P. Wu et al., "*Methodology for Synthesizing Crystalline Metallosilicates With Expanded Pore Windows Through Molecular Alkoxysilylation of Zeolitic Lamellar Precursors*", J. Am. Chem. Soc., 2008, vol. 130, pp. 8178-8187.

R. Young, "*The Rietveld Method*", Oxford Univ. Press, Oxford, 1995, p. 11.

L. Zhicheng et al., "*Static Synthesis of High-Quality MCM-22 Zeolite With High $SiO_2/Al_2O_3$ Ratio*", Chinese Science Bulletin, 2004, vol. 49, No. 6, pp. 556-561.

"*Periodic Table of the Elements*", Chemical and Engineering News, 1985, vol. 63, No. 5, p. 27.

J. Raun et al., "*Structure Investigation of Novel 3-D Crystalline Silicates From Layered Precursors*," 15 IZC Conference, Beijing, Book of Abstracts (2007).

W. Meier, et al., "*Atlas of Zeolite Framework Types*", Elsevier, Fifth Edition, 2001.

C. Gilmore et al., "A Multisolution Method of Phase Determination by Combined Maximization of Entropy and Likelihood. II. Application to Small Molecules", Acta Cryst., 1990, A46, pp. 297-308.

M. Leonowicz et al., "MCM-22: A Molecular Sieve with Two Independent Multidimensional Channel Systems", Science, vol. 264, Jun. 24, 1994, pp. 1910-1913.

PROCESS OF MAKING ALKYLAROMATICS USING EMM-13

PRIORITY CLAIM

This application is a National Stage Application of International Application No. PCT/US2009/050724 filed Jul. 15, 2009, which claims the benefit of U.S. Provisional Application Ser. No. 61/084,171 filed Jul. 28, 2008, both of which is are hereby incorporated by reference in their entirety.

FIELD OF THE INVENTION

The present disclosure relates to a process for producing alkylaromatics, especially mono-alkylaromatic compounds, for example ethylbenzene, cumene and sec-butylbenzene, using a molecular sieve composition designated as EMM-13 which is an MCM-22 family material having unique XRD features.

BACKGROUND OF THIS DISCLOSURE

Molecular sieve materials, both natural and synthetic, have been demonstrated in the past to have catalytic properties for various types of hydrocarbon conversion. Molecular sieves that find application in catalysis include any of the naturally occurring or synthetic crystalline molecular sieves. Examples of these zeolites include large pore zeolites, intermediate pore size zeolites, and small pore zeolites. These zeolites and their isotypes are described in "Atlas of Zeolite Framework Types", eds. W. H. Meier, D. H. Olson and Ch. Baerlocher, Elsevier, Fifth Edition, 2001, which is hereby incorporated by reference. A large pore zeolite generally has a pore size at least about 7 Å and includes LTL, VFI, MAZ, FAU, OFF, *BEA, and MOR framework type zeolites (IUPAC Commission of Zeolite Nomenclature). Examples of large pore zeolites include mazzite, offretite, zeolite L, VPI-5, zeolite Y, zeolite X, omega, and Beta. An intermediate pore size zeolite generally has a pore size from about 5 Å to less than about 7 Å and includes, for example, MFI, MEL, EUO, MTT, MFS, AEL, AFO, HEU, FER, MWW, and TON framework type zeolites (IUPAC Commission of Zeolite Nomenclature). Examples of intermediate pore size zeolites include ZSM-5, ZSM-11, ZSM-22, MCM-22, silicalite 1, and silicalite 2. A small pore size zeolite has a pore size from about 3 Å to less than about 5.0 Å and includes, for example, CHA, ERI, KFI, LEV, SOD, and LTA framework type zeolites (IUPAC Commission of Zeolite Nomenclature). Examples of small pore zeolites include ZK-4, ZSM-2, SAPO-34, SAPO-35, ZK-14, SAPO-42, ZK-21, ZK-22, ZK-5, ZK-20, zeolite A, chabazite, zeolite T, gmelinite, ALPO-17, and clinoptilolite.

U.S. Pat. No. 4,439,409 refers to a crystalline molecular sieve composition of matter named PSH-3 and its synthesis from a reaction mixture for hydrothermal reaction containing hexamethyleneimine, an organic compound which acts as directing agent for synthesis of the MCM-56 (U.S. Pat. No. 5,362,697). Hexamethyleneimine is also taught for use in synthesis of crystalline molecular sieves MCM-22 (U.S. Pat. No. 4,954,325) and MCM-49 (U.S. Pat. No. 5,236,575). A molecular sieve composition of matter referred to as zeolite SSZ-25 (U.S. Pat. No. 4,826,667) is synthesized from a reaction mixture for hydrothermal reaction containing an adamantane quaternary ammonium ion. U.S. Pat. No. 6,077,498 refers to a crystalline molecular sieve composition of matter named ITQ-1 and its synthesis from a reaction mixture for hydrothermal reaction containing one or a plurality of organic additives.

U.S. patent application Ser. No. 11/823,129 discloses a novel molecular sieve composition designated as EMM-10-P, having, in its as-synthesized form, an X-ray diffraction pattern including d-spacing maxima at 13.18±0.25 and 12.33±0.23 Angstroms, wherein the peak intensity of the d-spacing maximum at 13.18±0.25 Angstroms is at least as great as 90% of the peak intensity of the d-spacing maximum at 12.33±0.23 Angstroms. U.S. patent application Ser. No. 11/824,742 discloses a novel molecular sieve composition designated as EMM-10, in its ammonium exchanged form or in its calcined form, comprising unit cells with MWW topology, said crystalline molecular sieve is characterized by diffraction streaking from the unit cell arrangement in the c direction. The crystalline molecular sieve is further characterized by the arced hk0 patterns of electron diffraction pattern. The crystalline molecular sieve is further characterized by the streaks in the electron diffraction pattern along the c* direction. U.S. patent application Ser. No. 11/827,953 discloses a novel crystalline MCM-22 family molecular sieve having, in its as-synthesized form, an X-ray diffraction pattern including a peak at d-spacing maximum of 12.33±0.23 Angstroms, a distinguishable peak at a d-spacing maximum between 12.57 to about 14.17 Angstroms and a non-discrete peak at a d-spacing maximum between 8.8 to 11.0 Angstroms, wherein the peak intensity of the d-spacing maximum between 12.57 to about 14.17 Angstroms is less than 90% of the peak intensity of the d-spacing maximum at 12.33±0.23 Angstroms.

The term "MCM-22 family material" (or "material of the MCM-22 family" or "molecular sieve of the MCM-22 family"), as used herein, includes:

(i) molecular sieves made from a common first degree crystalline building block "unit cell having the MWW framework topology". A unit cell is a spatial arrangement of atoms which is tiled in three-dimensional space to describe the crystal as described in the "Atlas of Zeolite Framework Types", Fifth edition, 2001, the entire content of which is incorporated as reference;

(ii) molecular sieves made from a common second degree building block, a 2-dimensional tiling of such MWW framework type unit cells, forming a "monolayer of one unit cell thickness", preferably one c-unit cell thickness;

(iii) molecular sieves made from common second degree building blocks, "layers of one or more than one unit cell thickness", wherein the layer of more than one unit cell thickness is made from stacking, packing, or binding at least two monolayers of one unit cell thick of unit cells having the MWW framework topology. The stacking of such second degree building blocks can be in a regular fashion, an irregular fashion, a random fashion, or any combination thereof; or (iv) molecular sieves made by any regular or random 2-dimensional or 3-dimensional combination of unit cells having the MWW framework topology.

The MCM-22 family materials are characterized by having an X-ray diffraction pattern including d-spacing maxima at 12.4±0.25, 3.57±0.07 and 3.42±0.07 Angstroms (either calcined or as-synthesized). The MCM-22 family materials may also be characterized by having an X-ray diffraction pattern including d-spacing maxima at 12.4±0.25, 6.9±0.15, 3.57±0.07 and 3.42±0.07 Angstroms (either calcined or as-synthesized). The X-ray diffraction data used to characterize the molecular sieve are obtained by standard techniques using the K-alpha doublet of copper as the incident radiation and a diffractometer equipped with a scintillation counter and associated computer as the collection system. Materials belong to the MCM-22 family include MCM-22 (described in U.S. Pat. No. 4,954,325), PSH-3 (described in U.S. Pat. No. 4,439, 409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), ITQ-30 (described in International Patent Publication No. WO2005118476), MCM-36 (described in U.S. Pat. No. 5,250,277), MCM-49 (described in U.S. Pat. No. 5,236,575) and MCM-56 (described in U.S. Pat. No. 5,362,697). The entire contents of the patents are incorporated herein by reference.

It is to be appreciated the MCM-22 family molecular sieves described above are distinguished from conventional large pore zeolite alkylation catalysts, such as mordenite, in that the MCM-22 materials have 12-ring surface pockets which do not communicate with the 10-ring internal pore system of the molecular sieve.

The zeolitic materials designated by the IZA-SC as being of the MWW topology are multi-layered materials which have two pore systems arising from the presence of both 10 and 12 membered rings. The Atlas of Zeolite Framework Types classes five differently named materials as having this same topology: MCM-22, ERB-1, ITQ-1, PSH-3, and SSZ-25.

The MCM-22 family molecular sieves have been found to be useful in a variety of hydrocarbon conversion processes. Examples of MCM-22 family molecular sieve are MCM-22, MCM-49, MCM-56, ITQ-1, PSH-3, SSZ-25, and ERB-1. Such molecular sieves are useful for alkylation of aromatic compounds. For example, U.S. Pat. No. 6,936,744 discloses a process for producing a mono-alkylaromatic aromatic compound, particularly cumene, comprising the step of contacting a polyalkylated aromatic compound with an alkylatable aromatic compound under at least partial liquid phase conditions and in the presence of a transalkylation catalyst to produce the mono-alkylaromatic aromatic compound, wherein the transalkylation catalyst comprises a mixture at least two different crystalline molecular sieves, wherein each of the molecular sieves is selected from zeolite beta, zeolite Y, mordenite and a material having an X-ray diffraction pattern including d-spacing maxima at 12.4±0.25, 6.9±0.15, 3.57±0.07 and 3.42±0.07 Angstroms.

A report by J. Ruan, P. Wu, B. Slater, L. Wu, J. Xiao, Y. Liu, M. He, O. Terasaki at the 15 IZA Conference in Beijing in 2007 disclosed ISE-MWW and ISE-FER materials, the former made from MCM-22-P material as starting material. U.S. Patent Application Publication 2005/0158238 to Tatsumi et al. disclosed MWW type zeolite substance. U.S. Patent Application Publication 2004/0092757 to Oguchi et al. disclosed crystalline MWW type titanosilicate catalyst. A report by W. Fan, P. Wu, S, Namba, and T. Tatsumi (J. Catalyst 243 (2006) 183-191) disclosed a new titanosilicate molecular sieve with the structure analogous to MWW-type lamellar precursor. J. Ruan, P. Wu B. Slater and O. Terasaki disclosed detailed structure of Ti—YNU-1 (Angew. Chem. Int. Ed., 2005, 44, 6719) similar to ISE-MWW. Another report by P. Wu, J. Ruan, L. Wang, L. Wu, Y. Wang, Y. Liu, W. Fan. M. He, O. Terasaki and T. Tatsumi disclosed a methodology for synthesizing crystalline aluminosilicates with expanded pore windows through molecular alkoxysilylation of zeolitic lamellar precursors (J. Am. Chem. Soc. 2008, 130, 8178-8187).

These closely related material may further be distinguished by comparing XRD diffraction pattern for d-spacing maxima corresponding to (002), (100), (101) and (102) reflections for both as-synthesized and calcined materials. The d-spacing maximum corresponding to (002) reflection is typically in the range from 14.17 to 12.57 Angstroms (~6.15-7.05 deg 2-θ Cu Kα). The d-spacing maximum corresponding to (100) reflection is typically in the range from 12.1 to 12.56 Angstroms (~7.3-7.05 deg 2-θ Cu Kα). The d-spacing maximum corresponding to (101) reflection is typically in the range from 10.14 to 12.0 Angstroms (8.7-7.35 deg 2-θ Cu Kα). The d-spacing maximum corresponding to (102) reflection is typically in the range from 8.66 to 10.13 Angstroms (10.2-8.7 deg 2-θ Cu Kα). The following table (Table 1) summarized the differences between MCM-22, MCM-49, EMM-10, MCM-56 and the titanosilicate material reported by Tatsumi et al. based on the existence and/or the feature of XRD diffraction pattern for d-spacing maxima corresponding to (002), (100), (101) and (102) reflections for both as-synthesized and calcined materials.

TABLE 1

| XRD | As-synthesized | | | | Calcined | | | |
|---|---|---|---|---|---|---|---|---|
| | (002) | (100) | (101) | (102) | (002) | (100) | (101) | (102) |
| MCM-22 | MCM-22-P | | | | MCM-22 | | | |
| | Yes | Yes | Yes | Yes | No | Yes | Yes | Yes |
| | All four peaks are resolved. A valley exists between (101) and (102), wherein the measured intensity corrected for background at the lowest point being less than 50% of the point at the same XRD d-spacing on the line connecting maxima for (101) and (102). | | | | Peak corresponding to (002) is not visible. All other three peaks are resolved. A valley exists between (101) and (102), wherein the measured intensity corrected for background at the lowest point being less than 50% of the point at the same XRD d-spacing on the line connecting maxima for (101) and (102). | | | |
| EMM-10 | EMM-10-P | | | | EMM-10 | | | |
| | Yes | Yes | Non-discrete | | Yes | Yes | Non-discrete | |
| | Both (002) peak and (100) peak are resolved, wherein the peak intensity for (002) is at least as great as 90% of the peak intensity of the d-spacing maximum for (100). Further, peaks corresponding to (101) and (102) are non-discrete or exhibit a valley but with measured intensity corrected for background at the lowest point being not less than 50% of the point at the same XRD d-spacing on the line connecting maxima for (101) and (102). | | | | Peak corresponding to (002) is not visible. Peak corresponding to (100) is well resolved. And, peaks corresponding to (101) and (102) are non-discrete or exhibit a valley but with measured intensity corrected for background at the lowest point being not less than 50% of the point at the same XRD d-spacing on the line connecting maxima for (101) and (102). | | | |

TABLE 1-continued

| XRD | As-synthesized | | | | Calcined | | | |
|---|---|---|---|---|---|---|---|---|
| | (002) | (100) | (101) | (102) | (002) | (100) | (101) | (102) |
| MCM-22 family material as disclosed in U.S. Patent App. No. 11/827,953 | As-synthesized | | | | Calcined | | | |
| | Yes | Yes | Yes | Yes | No | Yes | Yes | Yes |
| | Peaks corresponding to (002) and (100) are well resolved. And, peaks corresponding to (101) and (102) are non-discrete peaks at a d-spacing maximum between 8.8 to 11 Angstroms, wherein the peak intensity of the (002) is less than 90% of the peak intensity of the (100) | | | | Peak corresponding to (002) is not visible. All other three peaks are resolved. A valley exists between (101) and (102), wherein the measured intensity corrected for background at the lowest point being less than 50% of the point at the same XRD d-spacing on the line connecting maxima for (101) and (102) | | | |
| MCM-49 | MCM-49-P | | | | MCM-49 | | | |
| | No | Yes | Yes | Yes | No | Yes | Yes | Yes |
| | Peak corresponding to (002) is not visible or as a shoulder peak. Peak corresponding to (100) is well resolved. And, peaks corresponding to (101) and (102) are resolved or exhibit a valley but with measured intensity corrected for background at the lowest point being not greater than 50% of the point at the same XRD d-spacing on the line connecting maxima for (101) and (102). | | | | Peak corresponding to (002) is not visible or as a shoulder peak. Peak corresponding to (100) is well resolved. And, peaks corresponding to (101) and (102) are resolved or exhibit a valley but with measured intensity corrected for background at the lowest point being not greater than 50% of the point at the same XRD d-spacing on the line connecting maxima for (101) and (102). | | | |
| MCM-56 | MCM-56-P | | | | MCM-56 | | | |
| | No | Yes | non-discrete | | No | Yes | non-discrete | |
| | Peak corresponding to (002) is not visible. Peak corresponding to (100) is well resolved. Peaks corresponding to (101) and (102) are non-discrete scattering. | | | | Peak corresponding to (002) is not visible. Peak corresponding to (100) is well resolved. Peaks corresponding to (101) and (102) are non-discrete or exhibit a valley but with measured intensity corrected for background at the lowest point being not less than 50% of the point at the same XRD d-spacing on the line connecting maxima for (101) and (102). | | | |
| MWW material | Precursor (US20050158238, FIG. 4) | | | | Calcined (US20050158238 FIG. 2) | | | |
| | Yes | Yes | Yes | Yes | No | Yes | Yes | Yes |
| | All four peaks are resolved. A valley exists between (101) and (102), wherein the measured intensity corrected for background at the lowest point being less than 50% of the point at the same XRD d-spacing on the line connecting maxima for (101) and (102). | | | | Only three peaks are resolved. A valley exists between (101) and (102), wherein the measured intensity corrected for background at the lowest point being less than 50% of the point at the same XRD d-spacing on the line connecting maxima for (101) and (102). | | | |
| Ti-MCM-22 | Precursor (J. Catal., Table 1) | | | | Calcined (US20050158238 FIG. 1) | | | |
| | Yes | Yes | Yes | Yes | Yes/No | Yes | Yes | Yes |
| | All four peaks reported for Si/Ti = 106. | | | | All four peaks are resolved for Si/Ti higher than 70. Only three peaks for Si/Ti less than 70. A valley exists between (101) and (102), wherein the measured intensity corrected for background at the lowest point being less than 50% of the point at the same XRD d-spacing on the line connecting maxima for (101) and (102). | | | |

It is known that crystal morphology, size and aggregation/agglomeration, or new x-ray diffraction can affect catalyst behavior, especially regarding catalyst activity and stability.

The alkylaromatic compounds, for example ethylbenzene and cumene, are valuable commodity chemicals which are used industrially for the production of styrene monomer and co-production of phenol and acetone respectively. In fact, a common route for the production of phenol comprises a process which involves alkylation of benzene with propylene to produce cumene, followed by oxidation of the cumene to the corresponding hydroperoxide, and then cleavage of the hydroperoxide to produce equal molar amounts of phenol and acetone. Ethylbenzene may be produced by a number of different chemical processes. One process which has achieved a significant degree of commercial success is the vapor phase alkylation of benzene with ethylene in the presence of a solid, acidic ZSM-5 zeolite catalyst. Examples of such ethylbenzene production processes are described in U.S. Pat. Nos. 3,751,504 (Keown), 4,547,605 (Kresge) and 4,016,218 (Haag).

Another process which has achieved significant commercial success is the liquid phase process for producing ethylbenzene from benzene and ethylene since it operates at a lower temperature than the vapor phase counterpart and hence tends to result in lower yields of by-products. For example, U.S. Pat. No. 4,891,458 (Innes) describes the liquid phase synthesis of ethylbenzene with zeolite Beta, whereas U.S. Pat. No. 5,334,795 (Chu) describes the use of MCM-22 in the liquid phase synthesis of ethylbenzene.

Cumene has for many years been produced commercially by the liquid phase alkylation of benzene with propylene over a Friedel-Crafts catalyst, particularly solid phosphoric acid or aluminum chloride. More recently, however, zeolite-based catalyst systems have been found to be more active and selective for propylation of benzene to cumene. For example, U.S. Pat. No. 4,992,606 (Kushnerick) describes the use of MCM-22 in the liquid phase alkylation of benzene with propylene.

Existing alkylation processes for producing alkylaromatic compounds, for example ethylbenzene and cumene, inherently produce polyalkylated species as well as the desired monoalkyated product. It is therefore normal to transalkylate the polyalkylated species with additional aromatic feed, for example benzene, to produce additional mono-alkylaromatic product, for example ethylbenzene or cumene, either by recycling the polyalkylated species to the alkylation reactor or, more frequently, by feeding the polyalkylated species to a separate transalkylation reactor. Examples of catalysts which have been used in the alkylation of aromatic species, such as alkylation of benzene with ethylene or propylene, and in the transalkylation of polyalkylated species, such as polyethylbenzenes and polyisopropylbenzenes, are listed in U.S. Pat. No. 5,557,024 (Cheng) and include MCM-49, MCM-22, PSH-3, SSZ-25, zeolite X, zeolite Y, zeolite Beta, acid dealuminized mordenite and TEA-mordenite. Transalkylation over a small crystal (<0.5 micron) form of TEA-mordenite is also disclosed in U.S. Pat. No. 6,984,764 (Roth et al).

Where the alkylation step is performed in the liquid phase, it is also desirable to conduct the transalkylation step under liquid phase conditions. However, by operating at relatively low temperatures, liquid phase processes impose increased requirements on the catalyst, particularly in the transalkylation step where the bulky polyalkylated species must be converted to additional mono-alkylaromatic product without producing unwanted by-products. This has proven to be a significant problem in the case of cumene production where existing catalysts have either lacked the desired activity or have resulted in the production of significant quantities of by-products such as ethylbenzene and n-propylbenzene.

There is, therefore, a need for a new process of producing mono-alkylaromatic compounds with crystalline molecular sieve.

SUMMARY OF THIS DISCLOSURE

In some embodiments, this disclosure relates to an alkylation process of producing mono-alkylaromatic compounds using a catalyst comprising EMM-13 molecular sieve, wherein the EMM-13 molecular sieve has, in its as-synthesized form, and in calcined form, an X-ray diffraction pattern including peaks having a d-spacing maximum in the range of 14.17 to 12.57 Angstroms (~6.15-7.05 deg 2-θ), a d-spacing maximum in the range of 12.1 to 12.56 Angstroms (~7.3-7.05 deg 2-θ), a d-spacing maximum in the range of 10.14 to 12.0 Angstroms (8.7-7.35 deg 2-θ), and a d-spacing maximum in the range from 8.66 to 10.13 Angstroms (10.2-8.7 deg 2-θ); wherein said peaks having d-spacing maximum in the range of 10.14 to 12.0 Angstroms (8.7-7.35 deg 2-θ) and d-spacing maximum in the range from 8.66 to 10.13 Angstroms (10.2-8.7 deg 2-θ) exhibit a valley in between, wherein the measured intensity corrected for background at the lowest point of said valley is less than 50% of the intensity point at the same XRD d-spacing on the line connecting said peaks having d-spacing maxima in the range of 10.14 to 12.0 Angstroms (8.7-7.35 deg 2-θ) and in the range from 8.66 to 10.13 Angstroms (10.2-8.7 deg 2-θ); wherein said EMM-13 molecular sieve has less than 1.6 wt. % Ti.

In some embodiments, this disclosure relates to an alkylation process of producing mono-alkylaromatic compounds using a catalyst comprising EMM-13 molecular sieve, wherein the EMM-13 molecular sieve has, in its as-synthesized form and in calcined form, an X-ray diffraction pattern including peaks at d-spacing maxima at 13.18±0.25, 12.33±0.23, 11.06±0.18 and 9.25±0.13 Angstroms, wherein said peaks at 11.06±0.18 and 9.25±0.13 Angstroms exhibit a valley in between the 11.06±0.18 and 9.25±0.13 Angstroms but with measured intensity corrected for background at the lowest point being less than 50% of the intensity point at the same XRD d-spacing on the line connecting d-spacing maxima at 11.06±0.18 and 9.25±0.13 Angstroms; wherein said EMM-13 molecular sieve has less than 1.6 wt. % Ti.

In other embodiments, the mono-alkylaromatic compounds comprise at least one of ethylbenzene, cumene and sec-butylbenzene.

In yet other embodiments, the process of this disclosure comprises contacting an alkylating agent with an alkylatable aromatic in the presence of a catalyst comprising EMM-13 under alkylation conditions to form mono-alkylaromatic compounds.

In other embodiments, the as-synthesized crystalline molecular sieve EMM-13 is further calcined under calcination conditions to form calcined EMM-13, wherein the calcination conditions comprise a temperature in the range of 300 to 700° C. for a time in the range of 1 min to 500 hours.

In some aspects, the EMM-13 molecular sieve further comprises, in its as-synthesized form and in calcined form, an X-ray diffraction pattern including peaks at 3.57±0.07 and 3.42±0.07 Angstroms.

In other aspects, the EMM-13 molecular sieve further comprises, in its as-synthesized form and in calcined form, an X-ray diffraction pattern including peak at 6.9±0.15.

In yet other aspects, the EMM-13 calcined molecular sieve has a composition involving the molar relationship:

$$X_2O_3:(n)YO_2,$$

wherein X is a trivalent element comprises at least one of aluminum, boron, iron and gallium, Y is a tetravalent element comprises at least one of silicon and germanium, and n is at least about 10. In the as-synthesized form the EMM-13 molecular sieve has a formula, on an anhydrous basis and in terms of moles of oxides per n moles of $YO_2$, as follows:

$$(0.005-1)M_2O:(1-4)R:X_2O_3 \cdot nYO_2$$

wherein M is an alkali or alkaline earth metal, and R is an organic moiety. In a preferred embodiment, n is from about 10 to about 150, more preferably from about 30 to about 60. In some preferred embodiment, X is aluminum and Y is silicon.

In some embodiments, the EMM-13 calcined molecular sieve has a collidine adsorption capacity at least 150 μmoles/g, preferably at least 250 μmoles/g.

These and other facets of the present invention shall become apparent from the following detailed description, FIGURES, and appended claims.

DETAILED DESCRIPTION

Introduction

All patents, patent applications, test procedures (such as ASTM methods, UL methods, and the like), priority documents, articles, publications, manuals, and other documents cited herein are fully incorporated by reference to the extent such disclosure is not inconsistent with the present invention and for all jurisdictions in which such incorporation is permitted.

When numerical lower limits and numerical upper limits are listed herein, ranges from any lower limit to any upper limit are contemplated. While the illustrative embodiments of the disclosure have been described with particularity, it will be understood that various other modifications will be apparent to and can be readily made by those skilled in the art without departing from the spirit and scope of the disclosure. Accordingly, it is not intended that the scope of the claims appended hereto be limited to the examples and descriptions set forth herein but rather that the claims be construed as encompassing all the features of patentable novelty which reside in the present disclosure, including all features which would be treated as equivalents thereof by those skilled in the art to which the disclosure pertains.

As used in this specification, the term "framework type" is used in the sense described in the "Atlas of Zeolite Framework Types," 2001.

As used herein, the numbering scheme for the Periodic Table Groups is used as in Chemical and Engineering News, 63(5), 27 (1985).

X-Ray Powder Diffraction Pattern

The interplanar spacings, d's, were calculated in Angstrom units (Å), and the relative intensities of the lines, $I/I_o$, where the intensity of the strongest line above background, $I_o$, is counted as 100, were derived with the use of a profile fitting routine (or second derivative algorithm). The intensities are uncorrected for Lorentz and polarization effects. The relative intensities are given in terms of the symbols VS=very strong (greater than 60 to 100), S=strong (greater than 40 to 60), M=medium (greater than 20 to 40) and W=weak (0 to 20). It should be understood that diffraction data listed as single lines may consist of multiple overlapping lines which under certain conditions, such as differences in crystallographic changes, may appear as resolved or partially resolved lines. Typically, crystallographic changes can include minor changes in unit cell parameters and/or a change in crystal symmetry, without a change in the structure. These minor effects, including changes in relative intensities, can also occur as a result of differences in cation content, framework composition, nature and degree of pore filling, and thermal and/or hydrothermal history. Other changes in diffraction patterns can be indicative of important differences between materials, which is the case for comparing MCM-22 with similar materials, e.g., MCM-49, MCM-56, and PSH-3.

The interplanar spacings, d's, were considered broad if they exhibited peak width of about 1.5° or more at half height determined as 50% intensity value from the peak maximum to the baseline.

The term "XRD distinguishable peak" as used herein is defined as XRD peak with clearly defined peak maximum, which is at least two times of the average background noise level.

The term "non-discrete" peaks (also "unresolved" peaks) in XRD as used herein means peaks having a monotonic profile in-between them (successive points either consistently increasing (or staying even) or decreasing (or staying even) within noise).

The term "discrete" peaks (also "resolved" peaks) in XRD as used herein means XRD peak(s) which are not non-discrete (unresolved).

Figure 1:
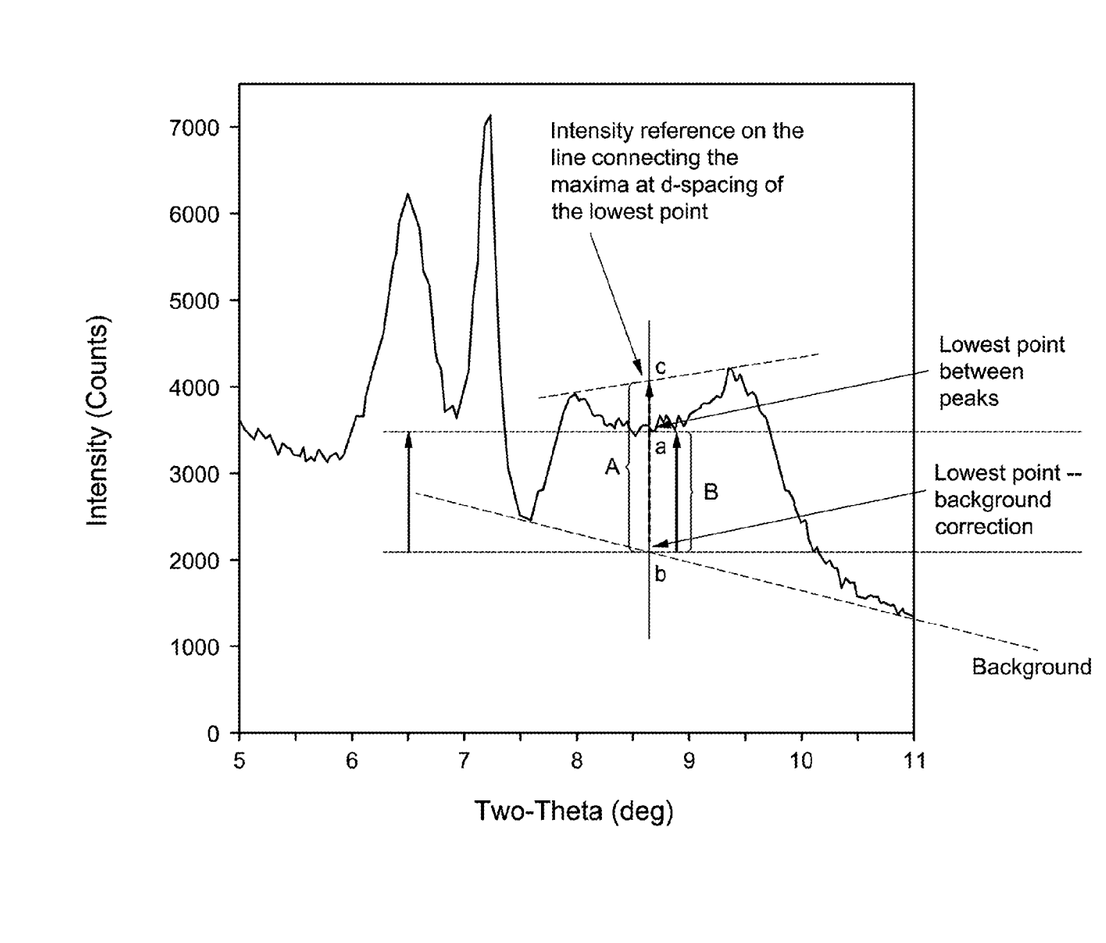
FIG. 1 shows the XRD pattern between 5 to 11 degree 2-θ of Example 1.

FIG. 1 graphically demonstrates the XRD pattern between 5 to 11 degree 2-θ of the product of Example 1. The measured intensity corrected for background at the lowest point between d-spacing maxima in the range of 10.14 to 12.0 Angstroms and in the range from 8.66 to 10.13 Angstroms, represented as B, is the distance between the lowest point (point a) and the point (point b) on the line of the background correction line at the same XRD d-spacing of the lowest point (point a). The distance between the point b and the point (point c) on the line connecting d-spacing maxima in the range of 10.14 to 12.0 Angstroms and in the range from 8.66 to 10.13 Angstroms at the same XRD d-spacing of the lowest point is represented as A.

Composition Matter of EMM-13

EMM-13 is a new MCM-22 family material with unprecedented XRD pattern indicating expanded structure and increased access to the interlayer region. It shows a unique distinctive combination of XRD features in the calcined form comprising peaks having a d-spacing maximum in the range of 14.17 to 12.57 Angstroms (~6.15-7.05 deg 2-θ), a d-spacing maximum in the range of 12.1 to 12.56 Angstroms (~7.3-7.05 deg 2-θ), a d-spacing maximum in the range of 10.14 to 12.0 Angstroms (8.7-7.35 deg 2-θ), and a d-spacing maximum in the range from 8.66 to 10.13 Angstroms (10.2-8.7 deg 2-θ); wherein said peaks having d-spacing maximum in the range of 10.14 to 12.0 Angstroms (8.7-7.35 deg 2-θ) and d-spacing maximum in the range from 8.66 to 10.13 Angstroms (10.2-8.7 deg 2-θ) exhibit a valley in between, wherein the measured intensity corrected for background at the lowest point of said valley is less than 50% of the intensity point at the same XRD d-spacing on the line connecting said peaks having d-spacing maxima in the range of 10.14 to 12.0 Angstroms (8.7-7.35 deg 2-θ) and in the range from 8.66 to 10.13 Angstroms (10.2-8.7 deg 2-θ); wherein said EMM-13 molecular sieve has less than 1.6 wt. % Ti.

In some embodiments, the composition matter of EMM-13 has, in as-synthesized form and in calcined form, an X-ray diffraction pattern including peaks at d-spacing maxima at 13.5±0.5, 12.33±0.23, and exhibit a valley in between the peaks at 11.05±0.2 and 9.31±0.2 Angstroms with measured intensity corrected for background at the lowest point being less than 50% of the point at the same XRD d-spacing on the line connecting d-spacing maxima at around 11.05±0.2 and 9.31±0.2 Angstroms, wherein said EMM-13 molecular sieve has less than 1.6 wt. % Ti.

In further embodiments, the composition matter of EMM-13 further has, in as-synthesized form and in calcined form, an X-ray diffraction pattern including peaks at d-spacing maxima at 3.57±0.06 and 3.43±0.06 Angstroms. In yet further embodiments, the composition matter of EMM-13 further has, in as-synthesized form and in calcined form, an X-ray diffraction pattern including peak at d-spacing maximum at 6.9±0.15 Angstroms. In yet further embodiments, the composition matter of EMM-13 further has, in as-synthesized form and in calcined form, an X-ray diffraction pattern including peak at d-spacing maximum at 3.96±0.08 Angstroms.

In other embodiments, the composition matter of EMM-13 has, in as-synthesized form and in calcined form, an X-ray diffraction pattern including peaks at d-spacing maxima and relative intensities at 13.5±0.5 (M-VS), 12.33±0.23 (M-VS), and exhibit a valley in between the peaks at 11.05±0.2 (W-S) and 9.31±0.2 (W-S) Angstroms but with measured intensity corrected for background at the lowest point being less than 50% of the point at the same XRD d-spacing on the line connecting d-spacing maxima at around 11.05±0.2 and 9.31±0.2 Angstroms.

TABLE 2

| Interplanar d-Spacing (Å) | Relative Intensity, $I/I_o \times 100$ |
|---|---|
| 14.17 > d > 12.57 | M-VS |
| 12.56 > d > 12.1 | M-VS |
| 12.0 > d > 10.14 | W-S |
| 10.13 > d > 8.66 | W-S |
| 6.9 ± 0.15 | W-M, broad |
| 3.96 ± 0.08 | W-VS, broad |
| 3.57 ± 0.06 | W-M |
| 3.43 ± 0.06 | M-VS |

In other embodiments, the composition matter of EMM-13 further has, in as-synthesized form and in calcined form, an X-ray diffraction pattern including peaks at d-spacing maxima at 3.57±0.06 (W-M) and 3.43±0.06 (M-VS) Angstroms. In yet further embodiments, the composition matter of EMM-13 further has, in as-synthesized form and in calcined form, an X-ray diffraction pattern including peak at d-spacing maximum at 6.9±0.15 Angstroms (W-M, broad). In yet further embodiments, the composition matter of EMM-13 further has, in as-synthesized form and in calcined form, an X-ray diffraction pattern including peak at d-spacing maximum at 3.96±0.08 Angstroms (W-VS, broad).

In some preferred embodiments, the X-ray diffraction pattern of the crystalline molecular sieve EMM-13 further has peaks at d-spacing maxima and intensities listed in Table 2.

In some embodiments, the X-ray diffraction pattern of the crystalline molecular sieve of this disclosure further includes a d-spacing maximum at 28±1 Angstroms.

In other embodiments, the composition matter of EMM-13 may be defined by its crystal structure. The crystal structure of EMM-13 may be defined by its unit cell, which is the smallest structural unit containing all the structural elements of the material. The unit cell of EMM-13 has P6/mmm space group and atomic coordinates of tetrahedral atoms (T) and oxygen atoms listed in Table 3 and with unit cell dimensions of a=14.198(2) and c=27.647(7) Å, wherein said EMM-13 molecular sieve has less than 1.6 wt. % Ti. Since the tetrahedral atoms may move about due to other crystal forces (presence of inorganic or organic species, for example), a range of ±0.05 nm is implied for each coordinate position.

TABLE 3

| Atom | x/a | y/b | z/c | Uiso | occ. |
|---|---|---|---|---|---|
| T1 | 0.6667 | 0.3333 | 0.1126(2) | 0.00649 | 1.0 |
| T2 | 0.4652(5) | 0.2326(3) | 0.1754(3) | | |
| T3 | 0.3901(5) | 0.0 | 0.1897(4) | | |
| T4 | 0.6667 | 0.3333 | 0.2403(4) | | |
| T5 | 0.6667 | 0.3333 | 0.3575(4) | | |
| T6 | 0.3894(5) | 0.0 | 0.3050(4) | | |
| T7 | 0.4215(5) | 0.2108(2) | 0.3593(3) | | |
| T8 | 0.2502(5) | 0.1251(3) | 0.4450(2) | | |
| T9 | 0.6667 | 0.3333 | 0.0 | | |
| O10 | 0.6667 | 0.3333 | 0.0562(1) | 0.010 | 1.0 |
| O11 | 0.5420(3) | 0.2710(1) | 0.1282(2) | | |
| O12 | 0.3876(5) | 0.1037(2) | 0.1681(4) | | |
| O13 | 0.5408(3) | 0.2704(2) | 0.2230(3) | | |
| O14 | 0.6667 | 0.3333 | 0.2991(4) | | |
| O15 | 0.3725(2) | 0.0 | 0.2473(3) | | |
| O16 | 0.5 | 0.0 | 0.176(1) | | |
| O17 | 0.5 | 0.0 | 0.318(1) | | |
| O18 | 0.3951(6) | 0.1062(3) | 0.3279(3) | | |
| O19 | 0.5453(3) | 0.2727(1) | 0.3786(4) | | |
| O20 | 0.3519(7) | 0.1759(4) | 0.4087(3) | | |

TABLE 3-continued

| Atom | x/a | y/b | z/c | Uiso | occ. |
|---|---|---|---|---|---|
| O21 | 0.1806(5) | 0.0 | 0.4320(3) | | |
| O22 | 0.2928(8) | 0.1464(4) | 0.5 | | |
| Extra-framework: | | | | | |
| T23 | 0.4499 | 0.1812 | 0.0686 | 0.025 | 0.355 |
| T24 | 0.2477 | 0.1232 | 0.0360 | 0.025 | 0.160 |
| Approximate | | | | | |
| O25 | 0.663 | 0.452 | 0.0 | 0.025 | 0.099 |

In Table 3, x/a, y/b, z/c are the fractional coordinates of the atoms in the unit cell referred to the unit cell axes a=b, c. Uiso is the isotropic temperature factor for each atom in Å$^2$. The quantity 'occ' is the occupancy factor for each atom, i.e., if less than 1.0, there is a statistical distribution of atoms or vacancies at each locus in the crystal.

In some embodiments, the EMM-13 calcined exhibits an extraordinary high collidine number greater than 150 µmoles/g, preferably greater than 200 µmoles/g, more preferably greater than 250 µmoles/g, even more preferably greater than 300 µmoles/g, and most preferably greater than 350 µmoles/g, compared to about 120-200 µmoles/g for EMM-10 and 120 µmoles/g for MCM-22. Not intended to be limited by any theory, we believe that the EMM-13 calcined has c-unit cell parameter fixed in the expanded form as the precursor when calcined.

Chemical Composition of as-Synthesized EMM-13 and Calcined EMM-13

The as-synthesized EMM-13 molecular sieve material of this disclosure may be prepared from an MCM-22-P precursor, which can be obtained from a reaction mixture for hydrothermal reaction containing sources of alkali or alkaline earth metal (M), e.g., sodium or potassium, cation, an oxide of trivalent element X, e.g., aluminum, an oxide of tetravalent element Y, e.g., silicon, an organic (R) directing agent, hereinafter more particularly described, and water, the reaction mixture for hydrothermal reaction having a composition, in terms of mole ratios of oxides:

$YO_2/X_2O_3$ in the range of 10 to infinity or in the range of 10 to 50;

$M/X_2O_3$ in the range of 0.005-5.0; and $R/X_2O_3$ in the range of 0.01-10.

The calcined EMM-13 molecular sieve material of this disclosure may be prepared by calcining as-synthesized EMM-13 under calcination conditions to remove at least the majority of the organic template R from the as-synthesized EMM-13.

The as-synthesized or calcined EMM-13 molecular sieve material has less than 1.6 wt. % titanium, preferably less than 1 wt. %, more preferably less than 0.5 wt. %, and most preferably less than 0.1 wt. % of titanium.

Process of Making EMM-13

In some embodiments, this disclosure relates to a method of manufacturing an as-synthesized crystalline molecular sieve EMM-13, the method comprising the steps of:
 (a) providing a mixture comprising MCM-22-P and acidic composition, optionally a spacing agent; and
 (b) treating the mixture at treatment conditions to form a product comprising as-synthesized EMM-13; and
 (c) recovering the acid treated crystalline molecular sieve.

In some preferred embodiments, the as-synthesized EMM-13 is made by a process comprising:
 (1) providing a mixture comprising MCM-22-P having $Si/Al_2$ in the range from 10-infinity, preferable from about 10 to 150, and acidic composition comprising at least one of nitric acid, sulfuric acid, hydrochloric acid; oxalic acid, wherein said acid has a concentration of less than or equal to 10 N, preferably less than 1N, optionally a spacing agent comprising at least one of dimethyldiethoxy silane, diethyldiethoxy silane, and tetraethyl silane (TEOS), preferable TEOS; and (2) treating the mixture of step (1) to treatment conditions, wherein the treatment conditions comprise a temperature in the range of 50-250° C. for a time in the range of 1-24 hrs, optionally with a stirring speed in the range of 0-1000 RPM.

The mixture of step (a) comprises MCM-22-P, acidic composition, and optionally a spacing agent, wherein the weight ratio of the solid content of the MCM-22-P over the acidic composition and the weight ratio of the spacing agent over the solid content of the MCM-22-P are listed in Table 4. The treatment conditions of step (b) include treatment temperature, treatment time. Useful and preferred ranges of the treatment temperature and treatment time are listed in Table 4.

TABLE 4

|  | Useful range | Preferred range | Most preferred range |
|---|---|---|---|
| Solid content (wt) Acidic composition | 0.001-1000 | 0.01-100 | 0.1-10 |
| Spacing agent (wt) Solid content (wt) | 0-2 | 0-1 | 0.01-0.5 |
| Acid concentration (N) | 0.001-10 | 0.001-5 | 0.01-2 |
| Temperature (° C.) | 25-250 | 50-200 | 90-170 |
| Time (hr) | 0.01-240 | 1-48 | 1-24 |

The following solid content over acidic composition weight ratios are useful lower limits: 0.001, 0.01, 0.05, 0.1, 0.5, 1, 5, 10, 50, 100 and 500. The following solid content over acidic composition weight ratios are useful upper limits: 0.01, 0.05, 0.1, 0.5, 1, 5, 10, 50, 100, 500 and 1000. The solid content over acidic composition weight ratio falls in a range between any one of the above-mentioned lower limits and any one of the above-mentioned upper limits, so long as the lower limit is less than or equal to the upper limit. The solid content over acidic composition weight ratio may be present in an amount ranging from 0.01 to 100 in one embodiment, alternatively 0.1 to 10, alternatively 0.1 to 5.

The following ratios are useful lower spacing agent over solid content weight ratio limits: 0, 0.001, 0.01, 0.05, 0.1, 0.5, 1, and 1.5. The following ratios are useful upper spacing agent over solid content weight ratio limits: 0.001, 0.01, 0.05, 0.1, 0.5, 1, 1.5, and 2. The spacing agent over solid content weight ratio falls in a range between any one of the above-mentioned lower spacing agent over solid content weight ratio limits and any one of the above-mentioned upper spacing agent over solid content weight ratio limits, so long as the lower spacing agent over solid content weight ratio limit is less than or equal to the upper spacing agent over solid content weight ratio limit. The spacing over solid content weight ratio may be present in an amount ranging from 0 to 2 in one embodiment, alternatively 0 to 1, and alternatively 0.1 to 0.5.

The following temperatures (° C.) are useful lower treatment temperature limits: 25, 50, 60, 70, 80, 90, 100, 110, 120, 130, 140, 150, 160, 170, and 200. The following temperatures (° C.) are useful upper treatment temperature limits: 50, 60, 70, 80, 90, 100, 110, 120, 130, 140, 150, 160, 170, 180, 190, 200, 210, 220, 230, 240, and 250. The treatment temperature (° C.) falls in a range between any one of the above-mentioned lower treatment temperature limits and any one of the above-mentioned upper treatment temperature limits, so long as the lower treatment temperature limit is less than or equal to the upper treatment temperature limit. The treatment temperature may be present in an amount ranging from 25° C. to 250° C. in one embodiment, alternatively 70° C. to 200° C., and alternatively 90° C. to 170° C.

The following times (hr) are useful lower time limits for treatment: 0.01, 1, 5, 10, 20, 30, 50, 100, and 150. The following times (hr) are useful upper time limits for treatment: 1, 5, 10, 20, 40, 50, 70, 100, 150, 200, and 240. The time (hr) for treatment falls in a range between any one of the above-mentioned lower time limits for treatment and any one of the above-mentioned upper time limits for treatment, so long as the lower time limit for treatment is less than or equal to the upper time limit for treatment. The time for treatment may be present in an amount ranging from 1 to 100 in one embodiment, alternatively 1 to 48, and alternatively 1 to 24.

(1) MCM-22-P

The MCM-22-P product is disclosed in U.S. Pat. No. 4,954,325. The entirety of which is incorporated herein by reference.

The MCM-22-P as disclosed by U.S. Pat. No. 4,954,325, may be made by crystallizing a mixture having a composition in molar ratio listed in Table 5.

TABLE 5

| Reactants | Useful | Preferred |
|---|---|---|
| $YO_2/X_2O_3$ | 10 to infinity | 15-55 |
| $H_2O/YO_2$ | 1 to 10000 | 5-35 |
| $OH^-/YO_2$* | 0.001-0.39 | 0.1-0.35 |
| $OH^-/YO_2$** | 0.001-0.59 | 0.1-0.5 |
| $M/YO_2$ | 0.001-2 | 0.1-1 |
| $R/YO_2$ | 0.001-2 | 0.01-0.5 |
| Seed*** | 0-25 wt % | 1-5 wt % |
| R | HMI | HMI |

After crystallization, the MCM-22-P product has a composition in molar ratio listed in Table 6.

TABLE 6

| Reactants | Useful | Preferred |
|---|---|---|
| $YO_2/X_2O_3$ | 10 to infinity | 10-150 |
| $M/X_2O_3$ | 0.005-0.1 | |
| $R/X_2O_3$ | 1-4 | |
| R | HMI | |

(2) Acidic Composition

The acidic composition useful for this disclosure comprises an acidic solute and a solvent. The acidic solute comprises at least one of inorganic acid, such as, nitric acid hydrochloric acid and sulfuric acid, and organic acid, such as, oxalic acid and acetic acid, or any combination of inorganic acid and organic acid. Preferably, the acidic solute is nitric acid. The solvent comprises at least one of water, methanol, ethanol, acetone and dimethylsulfone (DMSO).

The acid concentration of the acidic composition is in the range of 0.001 to 10. The following acid concentrations are useful lower limits: 0.001, 0.01, 0.05, 0.1, 0.5, 1, 2, 3, 4, 5, 6, 7, 8, and 9. The following acid concentrations are useful upper limits: 0.01, 0.05, 0.1, 0.5, 1, 2, 3, 4, 5, 6, 7, 8, 9, and 10. The acid concentration falls in a range between any one of the above-mentioned lower limits and any one of the above-mentioned upper limits, so long as the lower limit is less than or equal to the upper limit. The acid concentration may be present in an amount ranging from 0.001 to 5 in one embodiment, alternatively 0.01 to 4, and alternatively 0.1 to 2.

The weight of acidic composition as used in the solid content over acidic composition weight ratios is calculated based on the total weight of acidic solute and solvent.

(3) Spacing Agent

Optionally, the acidic treatment step also comprises a spacing agent. The spacing agent useful is any agent capable of providing a moiety that can stabilize the precursor in expanded form (i.e. having the distinct (002) peak at 13.5±0.25 in both as-synthesized and calcined forms). For example, the spacing agent may be a silylating agent which is capable of providing a silicon moiety that can stabilize the precursor in expanded form.

Examples of compounds for spacing include organo-compounds of a tetravalent element, a trivalent element, and/or a pentavalent element, such as, organosilicon compound, organogermanium compound, orgnaotitanium compounds, organoboron compounds, organoaluminum compound, and organophorphous compound. The organosilicon silicon compounds may comprise a polysiloxane include silicones, a siloxane, and a silane including disilanes and alkoxysilanes.

Silicone compounds that can be used in the present invention include the following:

wherein $R_1$ is hydrogen, fluoride, hydroxy, alkyl, aralkyl, alkaryl or fluoro-alkyl. The hydrocarbon substituents generally contain from 1 to about 10 carbon atoms and preferably are methyl or ethyl groups. $R_2$ is selected from the same group as $R_1$, and n is an integer at least 2 and generally in the range of 2 to about 1000. The molecular weight of the silicone compound employed is generally between about 80 to about 20,000 and preferably about 150 to about 10,000. Representative silicone compounds include dimethylsilicone, diethylsilicone, phenylmethylsilicone, methyl hydrogensilicone, ethylhydrogensilicone, phenylhydrogensilicone, fluoropropylsilicone, ethyltrifluoroprophysilicone, tetrachlorophenyl methyl methylethylsilicone, phenylethylsilicone, diphenylsilicone, methyltrisilicone, tetrachlorophenylethyl-silicone, methylvinylsilicone and ethylvinylsilicone. The silicone compound need not be linear but may be cyclic as for example hexamethylcyclotrisiloxane, octamethylcyclotetrasiloxane, hexaphenyl cyclotrisiloxane and octaphenylcyclotetrasiloxane. Mixtures of these compounds may also be used as well as silicones with other functional groups.

Useful siloxanes and polysiloxanes include as non-limiting example hexamethylcyclotrisiloxane, octamethylcyclotetrasiloxane, decamethylcyclopentasiloxane, hexamethyldisiloxane, octamethylrisiloxane, decamethyltetrasiloxane, hexaethylcyclotrisiloxane, octaethylcyclotetrasiloxane, hexaphenylcyclotrisiloxane and octaphenylcyclo-tetrasiloxane.

Useful silanes, disilanes, or alkoxysilanes include organic substituted silanes having the general formula:

wherein R is a reactive group such as hydrogen, alkoxy, halogen, carboxy, amino, acetamide, trialkylsilyoxy, $R_1$, $R_2$ and $R_3$ can be the same as R or can be an organic radical which may include alkyl of from 1 to about 40 carbon atoms, alkyl or aryl carboxylic acid wherein the organic portion of alkyl contains 1 to about 30 carbon atoms and the aryl group contains about 6 to about 24 carbons which may be further substituted, alkylaryl and arylalkyl groups containing about 7 to about 30 carbon atoms. Preferably, the alkyl group for an alkyl silane is between about 1 and about 4 carbon atoms in chain length. Mixtures may also be used.

The silanes or disilanes include, as non-limiting examples, dimethylphenylsilane, phenylrimethylsilane, triethylsilane and hexamethyldislane. Useful alkoxysilanes are those with at least one silicon-hydrogen bond.

Alkylation Process

The term "aromatic" in reference to the alkylatable aromatic compounds which may be useful as feedstock herein is to be understood in accordance with its art-recognized scope. This includes alkyl substituted and unsubstituted mono- and polynuclear compounds. Compounds of an aromatic character that possess a heteroatom may also be useful provided sufficient catalytic activity is maintained under the reaction conditions selected.

Substituted aromatic compounds that can be alkylated herein must possess at least one hydrogen atom directly bonded to the aromatic nucleus. The aromatic rings can be substituted with one or more alkyl, aryl, alkaryl, alkoxy, aryloxy, cycloalkyl, halide, and/or other groups that do not interfere with the alkylation reaction.

Suitable aromatic compounds include benzene, naphthalene, anthracene, naphthacene, perylene, coronene, and phenanthrene, with benzene being preferred.

Generally the alkyl groups that can be present as substituents on the aromatic compound contain from 1 to about 22 carbon atoms and usually from about 1 to 8 carbon atoms, and most usually from about 1 to 4 carbon atoms.

Suitable alkyl substituted aromatic compounds include toluene, xylene, isopropylbenzene, n-propylbenzene, alpha-methylnaphthalene, ethylbenzene, mesitylene, durene, cymenes, butylbenzene, pseudocumene, o-diethylbenzene, m-diethylbenzene, p-diethylbenzene, isoamylbenzene, isohexylbenzene, pentaethylbenzene, pentamethylbenzene; 1,2,3,4-tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalenes; ethylnaphthalene; 2,3-dimethylanthracene; 9-ethylanthracene; 2-methylanthracene; o-methylanthracene; 9,10-dimethylphenanthrene; and 3-methyl-phenanthrene. Higher molecular weight alkylaromatic compounds can also be used as starting materials and include aromatic organics such as are produced by the alkylation of aromatic organics with olefin oligomers. Such products are frequently referred to in the art as alkylate and include hexylbenzene, nonylbenzene, dodecylbenzene, pentadecylbenzene, hexyltoluene, nonyltoluene, dodecyltoluene, pentadecytoluene, etc. Very often alkylate is obtained as a high boiling fraction in which the alkyl group attached to the aromatic nucleus varies in size from about $C_6$ to about $C_{12}$. When cumene or ethylbenzene is the desired product, the present process produces acceptably little by-products such as n-propyl benzene and xylenes respectively. These by-products made in such instances may be less than about 100 wppm.

Reformate containing a mixture of benzene, toluene and/or xylene constitutes a particularly useful feed for the alkylation process of this disclosure.

The alkylating agents that may be useful in the process of this disclosure generally include any aliphatic or aromatic organic compound having one or more available alkylating aliphatic groups capable of reaction with the alkylatable aromatic compound, preferably with the alkylating group possessing from 1 to 5 carbon atoms. Examples of suitable alkylating agents are olefins such as ethylene, propylene, the butenes such as, for example, 1-butene, 2-butene or isobutylene, and the pentenes; alcohols (inclusive of monoalcohols, dialcohols, trialcohols, etc.) such as methanol, ethanol, the propanols, the butanols, and the pentanols; aldehydes such as formaldehyde, acetaldehyde, propionaldehyde, butyraldehyde, and n-valeraldehyde; and alkyl halides such as methyl chloride, ethyl chloride, the propyl chlorides, the butyl chlorides, and the pentyl chlorides, and so forth. Mixtures of these compounds may also be useful, such as, for example, propylene and propanol mixtures.

Mixtures of light olefins are useful as alkylating agents in the alkylation process of this disclosure. Accordingly, mixtures of ethylene, propylene, butenes, and/or pentenes which are major constituents of a variety of refinery streams, e.g., fuel gas, gas plant off-gas containing ethylene, propylene, etc., naphtha cracker off-gas containing light olefins, refinery FCC propane/propylene streams, etc., are useful alkylating agents. For example, a typical FCC light olefin stream possesses the following composition:

|  | Wt. % | Mole % |
|---|---|---|
| Ethane | 3.3 | 5.1 |
| Ethylene | 0.7 | 1.2 |
| Propane | 4.5 | 15.3 |
| Propylene | 42.5 | 46.8 |
| Isobutane | 12.9 | 10.3 |
| n-Butane | 3.3 | 2.6 |
| Butenes | 22.1 | 18.32 |
| Pentanes | 0.7 | 0.4 |

Reaction products that may be obtained from the process of the present disclosure include ethylbenzene from the reaction of benzene with ethylene, cumene from the reaction of benzene with propylene, ethyltoluene from the reaction of toluene with ethylene, cymenes from the reaction of toluene with propylene, and sec-butylbenzene from the reaction of benzene and n-butenes. Particularly preferred process mechanisms of the disclosure relate to the production of cumene by the alkylation of benzene with propylene and production of ethylbenzene by the alkylation of benzene with ethylene.

The reactants can be partially or completely in the liquid phase and can be neat, i.e. free from intentional admixture or dilution with other material, or they can be brought into contact with the catalyst composition with the aid of carrier gases or diluents such as, for example, hydrogen, methane and/or nitrogen.

The alkylation process of this disclosure may be conducted such that the organic reactants, i.e., the alkylatable aromatic compound and the alkylating agent, are brought into contact with the presently required catalyst in a suitable reaction zone under effective alkylation conditions. Such conditions include a temperature of from about 0° C. to about 500° C., preferably from about 10° C. to about 260° C., a pressure of from about 20 to about 25000 kPa-a, preferably from about 100 to about 5500 kPa-a, a molar ratio of alkylatable aromatic compound to alkylating agent of from about 0.1:1 to about 50:1, preferably from about 0.5:1 to about 10:1, and a feed weight hourly space velocity (WHSV) based on the alkylating agent of from about 0.1 to 500 hr$^{-1}$, preferably from about 0.1 to about 100 hr$^{-1}$.

When benzene is alkylated with ethylene to produce ethylbenzene, the alkylation reaction is preferably carried out in the liquid phase under conditions including a temperature of from about 150° C. to about 300° C., more preferably from about 170° C. to about 260° C.; a pressure up to about 20400 kPa-a, more preferably from about 2000 kPa-a to about 5500 kPa-a; a weight hourly space velocity (WHSV) based on the ethylene alkylating agent of from about 0.1 to about 20 hr$^{-1}$, more preferably from about 0.5 to about 6 hr$^{-1}$; and a ratio of benzene to ethylene in the alkylation reaction zone of from about 0.5:1 to about 100:1 molar, preferably 0.5:1 to 50:1 molar, more preferably from about 1:1 to about 30:1 molar, most preferably from about 1:1 to about 10:1 molar.

When benzene is alkylated with propylene to produce cumene, the reaction may also take place under liquid phase conditions including a temperature of up to about 250° C., preferably up to about 150° C., e.g., from about 10° C. to about 125° C.; a pressure of about 25000 kPa-a or less, e.g., from about 100 to about 3000 kPa-a; a weight hourly space velocity (WHSV) based on propylene alkylating agent of from about 0.1 hr$^{-1}$ to about 250 hr$^{-1}$, preferably from about 1 hr$^{-1}$ to about 50 hr$^{-1}$; and a ratio of benzene to propylene in the alkylation reaction zone of from about 0.5:1 to about 100:1 molar, preferably 0.5:1 to 50:1 molar, more preferably from about 1:1 to about 30:1 molar, most preferably from about 1:1 to about 10:1 molar.

When benzene is alkylated with a butene to produce sec-butylbenzene, the reaction may also take place under liquid phase conditions including a temperature of up to about 250° C., preferably up to about 150° C., e.g., from about 10° C. to about 125° C.; a pressure of about 25000 kPa-a or less, e.g., from about 1 to about 3000 kPa-a; a weight hourly space velocity (WHSV) based on the butene alkylating agent of from about 0.1 hr$^{-1}$ to about 250 hr$^{-1}$, preferably from about 1 hr$^{-1}$ to about 50 hr$^{-1}$; and a ratio of benzene to butene in the alkylation reaction zone of from about 0.5:1 to about 100:1 molar, preferably 0.5:1 to 50:1 molar, more preferably from about 1:1 to about 30:1 molar, most preferably from about 1:1 to about 10:1 molar.

A summary of the molecular sieves and/or zeolites, in terms of production, modification and characterization of molecular sieves, is described in the book "Molecular Sieves—Principles of Synthesis and Identification"; (R. Szostak, Blackie Academic & Professional, London, 1998, Second Edition). In addition to molecular sieves, amorphous materials, chiefly silica, aluminum silicate and aluminum oxide, have been used as adsorbents and catalyst supports. A number of long-known forming techniques, like spray drying, pilling, pelletizing and extrusion, have been and are being used to produce macrostructures in the form of, for example, spherical particles, extrudates, pellets and tablets of both micropores and other types of porous materials for use in catalysis, adsorption and ion exchange. A summary of these techniques is described in "Catalyst Manufacture," A. B. Stiles and T. A. Koch, Marcel Dekker, New York, 1995.

To the extent desired, the original metal cations of the as-synthesized material can be replaced in accordance with techniques well known in the art, at least in part, by ion exchange with other cations. Preferred replacing cations include metal ions, hydrogen ions, hydrogen precursor, e.g., ammonium, ions and mixtures thereof. Particularly preferred cations are those which tailor the catalytic activity for certain hydrocarbon conversion reactions. These include hydrogen, rare earth metals and metals of Groups 1-17, preferably Groups 2-12 of the Periodic Table of the Elements.

The EMM-13 crystalline molecular sieve of this disclosure should be generally dehydrated, at least partially. This can be done by heating to a temperature in the range of e.g., 200° C. to 595° C. in an atmosphere such as air or nitrogen, and at atmospheric, sub-atmospheric or super-atmospheric pressures for e.g., between 30 minutes and 48 hours. The degree of dehydration is measured by the percentage of weight loss relative to the total weight loss of a molecular sieve sample at 595° C. under flowing dry nitrogen (less than 0.001 kPa partial pressure of water vapor) for 48 hours. Dehydration can also be performed at room temperature (~25° C.) merely by placing the silicate in a vacuum, but a longer time is required to obtain a sufficient amount of dehydration.

The EMM-13 crystalline molecular sieve of this disclosure especially in its metal, hydrogen and ammonium forms can be beneficially converted to another form by thermal treatment. This thermal treatment is generally performed by heating one of these forms at a temperature at least 370° C. for at least one minute and generally not longer than 1000 hours. While subatmospheric pressure can be employed for the thermal treatment, atmospheric pressure is desired for reasons of convenience. The thermal treatment can be performed at a temperature up to about 925° C. The thermal treated product is particularly useful in the catalysis of certain hydrocarbon conversion reactions. The thermally treated product, especially in its metal, hydrogen and ammonium forms, is particularly useful in the catalysis of certain organic, e.g., hydrocarbon, conversion reactions. Non-limiting examples of such reactions include those described in U.S. Pat. Nos. 4,954,325; 4,973,784; 4,992,611; 4,956,514; 4,962,250; 4,982,033; 4,962,257; 4,962,256; 4,992,606; 4,954,663; 4,992,615; 4,983,276; 4,982,040; 4,962,239; 4,968,402; 5,000,839; 5,001,296; 4,986,894; 5,001,295; 5,001,283; 5,012,033; 5,019,670; 5,019,665; 5,019,664; and 5,013,422, each incorporated herein by reference as to the description of the catalytic reactions.

The EMM-13 crystalline molecular sieve of this disclosure can be shaped into a wide variety of particle sizes. Generally speaking, the particles can be in the form of a powder, a granule, or a molded product, such as an extrudate. In cases where the catalyst is molded, such as by extrusion, the crystals can be extruded before drying or partially dried and then extruded.

It is desired to incorporate the EMM-13 molecular sieve with another material resistant to the temperatures and other conditions employed in alkylation processes. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material in conjunction with the EMM-13 molecular sieve, i.e. combined therewith or present during synthesis of the EMM-13, which is active, tends to change the conversion and/or selectivity of the catalyst. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions. The materials, i.e. clays, oxides, etc., function as binders for the catalyst. It is desirable to provide a catalyst having good crush strength because in commercial use it is desirable to prevent the catalyst from breaking down into powder-like materials. These clay binders have been employed normally only for the purpose of improving the crush strength of the catalyst.

Naturally occurring clays which can be composited with the EMM-13 molecular sieve include the montmorillonite and kaolin family, which families include the subbentonites, and the kaolins commonly known as Dixie, McNamee, Georgia and Florida clays or others in which the main mineral constituent is halloysite, kaolinite, dictite, narcite, or anauxite. Such clays can be used in the raw state as originally mined or initially subjected to calcination, treatment or chemical modification. Binders useful for compositing with the present crystal also include inorganic oxides, notably alumina.

In addition to the foregoing materials, the EMM-13 molecular sieve can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of finely divided EMM-13 crystalline molecular sieve and inorganic oxide matrix vary widely, with the crystal content ranging from about 1 to about 99 percent by weight and more usually, particularly when the composite is prepared in the form of beads, in the range of about 20 to about 80 wt % of the composite.

The following examples reflect embodiments of the invention and are by no means intended to be limiting of the scope of the invention.

EXPERIMENTS

Powder X-ray Diffraction

Powder x-ray data were obtained on a Bruker D4 instrument in Bragg-Brentano geometry with monochromatic Cu Kα radiation; the pattern used for structural characterization extended from 1.2 to 80° in 2θ. Intensities for Rietveld refinement were extracted from the continuous scans. Indexing of powder patterns were carried out with the tool in the MDI Inc. program JADE.

Indexing of powder patterns were carried out with the tool in the MDI Inc. program JADE. After construction of a trial model (facilitated by the structure building module in Cerius$^2$ (Accelrys, Inc.)), its fit to the powder diffraction profile was made via Rietveld refinements with the program GSAS as described in A. C. Larsson & R. B. von Dreele, *General Structure Analysis System*, GSAS, Los Alamos National Laboratory, Los Alamos, N. Mex., 1994. Sometimes the framework would be optimized geometrically with the program DLS as described in Ch. Baerlocher, A. Hepp, & W. M. Meier, *Distance Least Squares Refinement Program, DLS-76*. ETH, Zürich, 1977. Electron density maps generated with GSAS could be used to locate additional atoms in the unit cell, tested first with Cerius$^2$ models to ensure that there would be no collision with framework atoms. Care was taken during refinements to avoid unusual bonding geometries. For the framework, this was partially ensured by imposing a restraint to the Si—O bond distances (1.61±0.03 Å) and O—O tetrahedral distances (2.65±0.06 Å). A weighting function for the framework refinement was gradually relaxed but, after each refinement step, the chemical reasonableness of the bonding geometry was ascertained. In addition to unit cell parameters, background and zero shift, profile functions were also refined to improve the model fit but it was sometimes seen that the usual R-values did not necessarily denote a close match of the model to the experimental intensity curve. In several cases, adjustments were made for preferred orientation, expected for Bragg-Brentano data from a platy crystal assembly according to R. A. Young, in: *The Rietveld Method* (R. A. Young, ed.). Oxford Univ. Press, Oxford, 1995, p. 11.

Surface Areas

The overall surface area of a molecular sieve may be measured by the Brunauer-Emmett-Teller (BET) method using adsorption-desorption of nitrogen (temperature of liquid nitrogen, 77 K). The internal surface area (ZSA, m$^2$/g) may be calculated using t-plot of the Brunauer-Emmett-Teller (BET) measurement. The external surface area (ZSA, m$^2$/g) is calculated by subtracting the internal surface area from the overall surface area measured by the Brunauer-Emmett-Teller (BET) measurement. Micro-pore volume (M-pore in cm$^3$/g) is determined by nitrogen adsorption/desorption (nitrogen isotherm).

Collidine Number Measurement

The collidine number of a molecular sieve may be measured by TGA, A sample is dried at 200° C. to constant weight (weight change less than ±1% for the period of 1 hour). The weight of the dried sample, the sorbate, is then measured. The sorbent, 2,4,6-collidine, is delivered by a sparger maintained at 3 Torr collidine partial pressure and carried over the sample by nitrogen passed 200 ml/min for 60 min. The collidine number is expressed as micromoles of adsorbed per gram of the sorbate.

Electron Microscopy and Diffraction

Selected area electron diffraction experiments were carried out at 300 kV with an FEI/Philips CM-30 electron microscope using a selected area diameter of 0.25 μm. In some cases, three-dimensional tilts were made around a defined reciprocal lattice to map out a 3-D reciprocal lattice. Bright field electron micrographs were obtained at 32,240× direct magnification. The field-limiting aperture passed diffraction information out to d*=0.08 Å$^{-1}$. All exposures were recorded on Kodak Biomax MS film.

For preliminary intensity data collection, diffraction films were digitized on a flat bed scanner and, after their indexing, the intensities of individual spots were estimated with the program ELD according to X. D. Zou, Yu. Sukharev & S. Hovmöller, (Ultramicroscopy 53 (1994) 271 within the CRISP as described in S. Hovmöller, Ultramicroscopy 41 (1992) 121) package. Symmetry-related reflections were averaged and no Lorentz correction was applied to the derived structure factor magnitudes. In some cases it was difficult to obtain suitable peak integration with ELD. In this case, films were scanned on a flat bed Joyce Loebl Mk. III microdensitometer and the peak areas used as an estimate of their intensities. For merging data into a three-dimensional set, common reflections from separate zones were used for scaling one set to the other as discussed in D. L. Dorset, *Structural Electron Crystallography*. Plenum, N.Y., 1995.

For electron diffraction studies, structure factor calculations were carried out with the Fortran program SF and one-dimensional electrostatic potential distributions were obtained with the Fortran program ZPOT after phase approximates from a known structure were provided.

Three-dimensional tilts around defined unit cell reciprocal axes (generally a*) were plotted to give an undistorted view of the three-dimensional reciprocal lattice. Using the usual gold powder standard for calibration, the dimensions of the complete unit cell could be measured. From systematic absences in these plots, the unit cell symmetry could also be estimated according to Th. Hahn (ed.), *International Tables for Crystallography. Volume A. Space-Group Symmetry*. Kluwer, Dordrecht, 1995.

Structures were found from a 3-D dataset using maximum entropy and likelihood with the program MICE according to C. J. Gilmore, K. Shankland, & G. Bricogne, Proc. Roy. Soc. London 442 (1993) 97. It is useful to utilize a typical zeolite density histogram as described in Ch. Baerlocher, L. B. McCusker & L. Palatinus, Z. Krist. 222 (2007) 47 to further discriminate among trial structural solutions culled by a maximum likelihood FIGURE of merit according to C. J. Gilmore, G Bricogne & C. Bannister, Acta Cryst. A46 (1990) 297. Instead of full factorial phase permutation of identified reflections, a Nordström-Robinson error correcting code according to C. J. Gilmore, W. Dong, & G Bricogne, Acta Cryst. A55 (1999) 70 was used to speed up the calculation.

Materials and Synthesis

Example 1

Synthesis of MCM-22-P with Si/Al2~60

The synthesis mixture was prepared with 184 g of water, 1.5 g of Usalco 45, 22 g of 10% NaOH, 17 g of hexamethyleneimine and 23 g of Ultrasil. It was reacted at 150° C. with 100 RPM in a 300 ml autoclave. Product composition and structural porosity characteristics are listed in Table 7.

Example 2

Synthesis of MCM-22-P with Si/Al2~23

The synthesis was analogous to Example 1, U.S. Pat. No. 4,954,325. Product composition and structural porosity characteristics are listed in Table 7.

Example 3a

Acid Treatment of MCM-22-P (Example 1) with Silane to Produce EMM-13 as-Synthesized and EMM-13 Calcined Mixing 30 grams of 1 M HNO$_3$ solution (obtained by mixing 3 g of concentrated acid with 27 g of water) with 0.3 g of spacing agent (silylating agent) dimethyldiethoxy silane, and followed with adding 3 g of as-synthesized MCM-22-P sample of Example 1. The mixture was reacted at 170° C. for 24 hrs. The product was filtered, washed with water and dried. The as-treated material was identified by XRD as EMM-13 as-synthesized. The as-treated material was further calcined in air at 540° C. for 4 hrs. The calcined material of example 3a was identified by XRD as EMM-13 calcined. Product composition and structural porosity characteristics are listed in Table 7.

Example 3b

Acid Treatment of MCM-22-P (Example 1) to Produce EMM-13 as-Synthesized and EMM-13 Calcined Mixing 30 grams of 1 M HNO$_3$ solution (obtained by mixing 3 g of concentrated acid with 27 g of water), and followed with adding 3 g of as-synthesized MCM-22-P sample of Example 1. The mixture was reacted at 170° C. for 24 hrs. The product was filtered, washed with water and dried. The as-treated material was identified by XRD as EMM-13 as-synthesized. The as-treated material was further calcined in air at 540° C. for 4 hrs. The calcined material of example 3b was identified by XRD as EMM-13 calcined. Product composition and structural porosity characteristics are listed in Table 7.

Example 3c

Acid Treatment of MCM-22-P (Example 1) with Silica to Produce EMM-13 as-Synthesized and EMM-13 Calcined Mixing 30 grams of 1 M $HNO_3$ solution (obtained by mixing 3 g of concentrated acid with 27 g of water) with 0.3 g of fumed silica (Cab-o-Sil), and followed with adding 3 g of as-synthesized MCM-22-P sample of Example 1. The mixture was reacted at 170° C. for 24 hrs. The product was filtered, washed with water and dried. The as-treated material was identified by XRD as EMM-13 as-synthesized. The as-treated material was further calcined in air at 540° C. for 4 hrs. The calcined material of example 3c was identified by XRD as EMM-13 calcined. Product composition and structural porosity characteristics are listed in Table 7.

Example 4a

Acid Treatment of MCM-22-P (Example 2) with Silane to Produce MCM-22-P and MCM-22

Mixing 30 grams of 1 M $HNO_3$ solution (obtained by mixing 3 g of concentrated acid with 27 g of water) with 0.3 g of spacing agent (silylating agent) dimethyldiethoxy silane, and followed with adding 3 g of as-synthesized MCM-22-P sample of Example 2. The mixture was reacted at 170° C. for 24 hrs. The product was filtered, washed with water and dried. The as-treated material was identified by XRD as MCM-22-P. The as-treated material was further calcined in air at 540° C. for 4 hrs. The calcined material of example 4a was identified by XRD as MCM-22. Product composition and structural porosity characteristics are listed in Table 7.

Example 4b

Acid Treatment of MCM-22-P (Example 1) to Produce MCM-22

Mixing 30 grams of 1 M $HNO_3$ solution (obtained by mixing 3 g of concentrated acid with 27 g of water), and followed with adding 3 g of as-synthesized MCM-22-P sample of Example 2. The mixture was reacted at 170° C. for 24 hrs. The product was filtered, washed with water and dried. The as-treated material was identified by XRD as MCM-22-P. The as-treated material was further calcined in air at 540° C. for 4 hrs. The calcined material of example 4b was identified by XRD as MCM-22. Product composition and structural porosity characteristics are listed in Table 7.

TABLE 7

| | 1 | 3a | 3b | 3c | 2 | 4a | 4b |
|---|---|---|---|---|---|---|---|
| Synthesis conditions | | | | | | | |
| $Si/Al_2$ | 87 | | | | 29.9 | | |
| Si + Al | 8.7 | | | | 13.9 | | |
| OH/Si | 0.18 | | | | 0.17 | | |
| R/Si | 0.49 | | | | 0.35 | | |
| T (C.) | 150 | | | | 150 | | |
| Time (hr) | 76 | | | | 60-70 | | |
| Acid treatment conditions | | | | | | | |
| T (° C.) | | 170 | 170 | 170 | | 170 | 170 |
| Time (hr) | | 24 | 24 | 24 | | 24 | 24 |
| Product Characterization and Properties | | | | | | | |
| XRD | MCM-22-P + trace ZSM-12 | EMM-13 as-synthesized | EMM-13 as-synthesized | EMM-13 as-synthesized | MCM-22-P | MCM-22-P | MCM-22-P |
| $Al_2O_3$ | 2.3 | 2.16 | 2.1 | | | | 4.88 |
| Na | 0.4 | 0.0339 | 0.267 | | | | 0.0789 |
| $SiO_2$ | 78.9 | 85.3 | 78.7 | | | | 76 |
| $Si/Al_2$ | 58.32 | 67.13 | 63.71 | | | | 26.48 |
| Product Characterization and Properties after Calcination in Air at 540° C. for 4 hrs | | | | | | | |
| XRD | MCM-22 | EMM-13 | EMM-13 | EMM-13 | MCM-22 | MCM-22 | MCM-22 |
| BET | 410 | 485 | 463 | 396 | | 436 | 472 |
| ZSA | 378 | 456 | 404 | 327 | | 329 | 362 |
| MSA | 32 | 29 | 58 | 68 | | 107 | 110 |
| M-pore | 0.152 | 0.18 | 0.16 | 0.13 | | 0.13 | 0.15 |
| Collidine | | 214 | 153 | | 124 | | |

Example 5

Synthesis of 40/1 MCM-22-P

The preparation was carried out like above but with a gel having the following molar ratio of reactants: silica/alumina=54/1, OH/Si=0.15, water/Si=35, R/Si=0.58. The mixture was heated at 170° C. for 70 hrs and product isolated by standard methods.

Examples 6-16

Synthesis EMM-13 with 40/1 MCM-22-P

Examples 6-16 were conducted by mixing concentrated acid with water to form acid solution according to Table 8. Various amount of spacing agent (silylating agent) dimethyldiethoxy silane, were added followed by as-synthesized MCM-22-P sample of Example 5 according to Table 8. The mixtures were reacted at treatment conditions including a treatment temperature and time according to Table 8. The products were filtered, washed with water and dried. Calcination of the products was carried out in air at 540° C. for 4 hrs. The as-treated materials were further calcined in air at 540° C. for 4 hrs. The calcined materials of Example 6-11 and 13-16 were identified by XRD as EMM-13.

Example 17

Three 65 wt. % EMM-13 calcined of Example 3a and 35 wt. % alumina catalyst were prepared. These three catalysts were tested for benzene alkylation with propylene to form cumene.

Test Sequence for Cumene Manufacture in a Fixed Bed Test

The experiment was conducted in a fixed bed 3/8" OD tubular reactor in a downflow configuration with an 1/8" internal thermocouple. The reactor furnace was controlled in isothermal mode. Two grams of catalyst sized to 14/20 mesh was loaded into the 3/8" reactor. The catalyst bed was axially centered in the middle furnace zone. The catalyst was packed with inert sand to fill the interstitial void spaces. Reaction conditions were 130° C., 2169 kPa-a and the benzene/propylene molar ratio was 3/1. Weight hourly space velocity was 1 $hr^{-1}$ on a propylene basis.

At reactor start-up, the reactor was brought to reaction pressure of 2169 kPa-a with the ultra high purity nitrogen, and heated to reaction temperature of 150° C. prior to introducing the benzene feed for 24 hours. The catalyst was allowed to equilibrate for 1 day prior to introducing the propylene to achieve steady state before data was collected. The reactor was cooled to 130° C. under benzene flow and then propylene was introduced. Products were collected and analyzed for 13

TABLE 8

| | Amount, grams | | | | | | Surface area, $m^2/g$ | | | |
|---|---|---|---|---|---|---|---|---|---|---|
| Example number | Water | Conc. HNO3 | 40/1 Si/Al2 MCM-22-P | Silane | Time, hours | Temp., ° C. | Tortal BET | Zeolite ZSA | Mesopore, MSA | Collidine µmole/g |
| Parent | | | 40/1 Si/Al2 MCM-22-P | | | | 521 | 478 | 43 | 44 |
| 6 | 9.5 | 0.5 | 0.4 | 0.02 | 24 | 170 | 568 | 485 | 83 | 350 |
| 7 | 7.25 | 2.75 | 1.7 | 0.21 | 17 | 145 | 600 | 540 | 60 | 244 |
| 8 | 9.5 | 0.5 | 3 | 0.02 | 10 | 170 | 615 | 544 | 71 | 262 |
| 9 | 5 | 5 | 0.4 | 0.02 | 10 | 120 | 642 | 573 | 69 | 195 |
| 10 | 5 | 5 | 0.4 | 0.4 | 10 | 170 | 492 | 462 | 30 | 134 |
| 11 | 9.5 | 0.5 | 3 | 0.4 | 10 | 120 | 623 | 565 | 58 | 327 |
| 12 | 5 | 5 | 3 | 0.02 | 24 | 120 | 556 | 480 | 76 | 89 |
| 13 | 9.5 | 0.5 | 0.4 | 0.4 | 24 | 120 | 533 | 499 | 34 | 266 |
| 14 | 5 | 5 | 3 | 0.4 | 24 | 170 | 675 | 609 | 66 | 311 |
| 15 | 7.25 | 2.75 | 1.7 | 0.21 | 17 | 145 | 609 | 547 | 62 | 245 |
| 16 | 8.62 | 1.38 | 3 | 0.5 | 17 | 90 | 642 | 588 | 55 | 212 |

Feed Pretreatment

Benzene

Benzene was obtained from a commercial source. The benzene was passed through a pretreatment vessel containing equal parts (by volume) molecular sieve 13X, molecular sieve 4A, Engelhard F-24 Clay, and Selexsorb CD (in order from inlet to outlet), and then through a pretreatment vessel containing MCM-22 catalyst. All feed pretreatment materials were dried in a 260° C. oven for 12 hours before using.

Propylene

Propylene was obtained from a commercial specialty gases source and were polymer grade.

Ethylene

Ethylene was obtained from a commercial specialty gases source and was polymer grade.

Nitrogen

Nitrogen was ultra high purity grade and obtained from a commercial specialty gases source.

days on-stream. Results shows that Diisopropylbenzene (DIPB) over cumene (isopropylbenzene, IPB) molar ratios of the products fall in the range of 12% to 18%.

Example 18

0.9 gram of pellet of 65 wt. % EMM-13 (Example 3a) and 35 wt. % Versal 300 alumina (commercially available from UOP) was used for benzene alkylation with ethylene to form ethylbenzene. The catalyst was calcined for 2 hours at 538° C.

Benzene alkylation with ethylene was conducted by charging a fixed weight of catalyst to a well-mixed Parr autoclave reactor along with a mixture comprising benzene and ethylene (benzene/ethylene ratio of 3.5 molar). The reaction was carried out at 220° C. and 3893 KPa-a (550 psig) for 4 hours. A small sample of the product was withdrawn at regular intervals and analyzed by gas chromatography. The catalyst performance was assessed by a kinetic activity rate constant and diethylbenzene/ethylbenzene weight ratio after 4 hours.

The EMM-13 catalyst has an activity of 3 (hr·gmole/cc)$^{-1}$ and a selectivity of 10.1 measured by diethylbenzene/ethylbenzene weight ratio.

We claim:

1. A process for manufacturing a mono-alkylaromatic aromatic compound, said process comprising contacting a feedstock comprising an alkylatable aromatic compound and an alkylating agent under alkylation reaction conditions with a EMM-13 catalyst, to form said mono-alkylaromatic compound, said EMM-13 catalyst comprising a molecular sieve having a framework of tetrahedral atoms (T) bridged by oxygen atoms (O), said tetrahedral atom framework being defined by a unit cell having dimensions of a=b=0.14198(2) and c=0.27647(7) in nanometers, wherein x/a, y/b, z/c are the fractional coordinates of each atom of said unit cell, Uiso is the isotropic temperature factor for each atom in Å$^2$(Angstrom units)$^2$, and the quantity 'occ' is the occupancy factor for each atom, said unit cell having atomic coordinates in nanometers shown in the following table:

| Atom | x/a | y/b | z/c | Uiso | occ. |
|---|---|---|---|---|---|
| T1 | 0.6667 | 0.3333 | 0.1126(2) | 0.00649 | 1.0 |
| T2 | 0.4652(5) | 0.2326(3) | 0.1754(3) | | |
| T3 | 0.3901(5) | 0.0 | 0.1897(4) | | |
| T4 | 0.6667 | 0.3333 | 0.2403(4) | | |
| T5 | 0.6667 | 0.3333 | 0.3575(4) | | |
| T6 | 0.3894(5) | 0.0 | 0.3050(4) | | |
| T7 | 0.4215(5) | 0.2108(2) | 0.3593(3) | | |
| T8 | 0.2502(5) | 0.1251(3) | 0.4450(2) | | |
| T9 | 0.6667 | 0.3333 | 0.0 | | |
| O10 | 0.6667 | 0.3333 | 0.0562(1) | 0.010 | 1.0 |
| O11 | 0.5420(3) | 0.2710(1) | 0.1282(2) | | |
| O12 | 0.3876(5) | 0.1037(2) | 0.1681(4) | | |
| O13 | 0.5408(3) | 0.2704(2) | 0.2230(3) | | |
| O14 | 0.6667 | 0.3333 | 0.2991(4) | | |
| O15 | 0.3725(2) | 0.0 | 0.2473(3) | | |
| O16 | 0.5 | 0.0 | 0.176(1) | | |
| O17 | 0.5 | 0.0 | 0.318(1) | | |
| O18 | 0.3951(6) | 0.1062(3) | 0.3279(3) | | |
| O19 | 0.5453(3) | 0.2727(1) | 0.3786(4) | | |
| O20 | 0.3519(7) | 0.1759(4) | 0.4087(3) | | |
| O21 | 0.1806(5) | 0.0 | 0.4320(3) | | |
| O22 | 0.2928(8) | 0.1464(4) | 0.5 | | |
| Extra-framework: | | | | | |
| T23 | 0.4499 | 0.1812 | 0.0686 | 0.025 | 0.355 |
| T24 | 0.2477 | 0.1232 | 0.0360 | 0.025 | 0.160 |
| Approximate | | | | | |
| O25 | 0.663 | 0.452 | 0.0 | 0.025 | 0.099. |

2. The process of claim 1, wherein said molecular sieve further has a composition involving the molar relationship:

$$X_2O_3{:}(n)YO_2,$$

wherein X is a trivalent element which comprises at least one of aluminum, boron, iron and gallium, Y is a tetravalent element which comprises at least one of silicon and germanium, and n is at least about 30.

3. The process of claim 1, wherein said molecular sieve further has, in the as-synthesized form, a formula, on an anhydrous basis and in terms of moles of oxides per n moles of $YO_2$, as follows:

$$(0.005\text{-}1)M_2O{:}(1\text{-}4)R{:}X_2O_3{:}nYO_2$$

wherein M is an alkali or alkaline earth metal, n is at least about 30, and R is an organic moiety.

4. The process of claim 2, wherein said n of said molecular sieve is from about 30 to about 150.

5. The process of claim 2, wherein said X of said molecular sieve is aluminum and said Y of said molecular sieve is silicon.

6. The process of claim 1, wherein said molecular sieve comprising less than 1 wt. % Ti.

7. The process of claim 1, wherein said molecular sieve having a collidine adsorption capacity at least 150 μmoles/g.

8. The process of claim 1, wherein said molecular sieve further has, in its as-synthesized form and in calcined form, an X-ray diffraction pattern including peaks at d-spacing maxima at 13.18±0.25, 12.33±0.23, 11.05±0.2 and 9.31±0.2 Angstroms, wherein said peaks at d-spacing maxima at 11.05±0.2 and 9.31±0.2 Angstroms exhibit a valley in between, and the measured intensity corrected for background at the lowest point of said valley is less than 50% of the intensity point at the same X-ray diffraction pattern d-spacing on the line connecting d-spacing maxima at 11.05±0.2 and 9.31±0.2 Angstroms.

9. The process of claim 8, wherein said molecular sieve further has, in its as-synthesized form and in calcined form, an X-ray diffraction pattern including peaks at 6.9±0.15, 3.57±0.07 and 3.42±0.07 Angstroms.

10. The process of claim 1, wherein said alkylatable aromatic compound is selected from the group consisting of benzene, naphthalene, anthracene, naphthacene, perylene, coronene, phenanthrene, xylene, n-propylbenzene, alpha-methylnaphthalene, o-diethylbenzene, m-diethylbenzene, p-diethylbenzene, pentaethylbenzene, pentamethylbenzene; 1,2,3,4-tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalenes; ethylnaphthalene; 2,3-dimethylanthracene; 9-ethylanthracene; 2-methylanthracene; o-methylanthracene; 9,10-dimethylphenanthrene; 3-methyl-phenanthrene and mixtures thereof.

11. The process of claim 1, wherein said alkylatable aromatic compound comprises at least one of benzene and naphthalene.

12. The process of claim 1, wherein said alkylating agent is selected from the group consisting of olefins, alcohols, aldehydes, alkyl halides and mixtures thereof.

13. The process of claim 1, wherein said alkylating agent comprises at least one of ethylene, propylene and butenes.

14. The process of claim 1, wherein said alkylation reaction conditions include a temperature of from about 0° C. to about 500° C., a pressure of from about 0.2 to about 25000 kPa-a, a molar ratio of alkylatable aromatic compound to alkylating agent of from about 0.1:1 to about 50:1, and a feed weight hourly space velocity (WHSV) based on the alkylating agent of from about 0.1 to 500 hr$^{-1}$.

15. The process of claim 1, wherein said alkylatable aromatic compound comprises benzene, said alkylating agent comprises ethylene, said mono-alkylaromatic aromatic compound comprises ethylbenzene, said alkylation reaction conditions include a temperature of from about 150° C. to about 300° C., a pressure of from about 2000 to about 5500 kPa-a, a molar ratio of alkylatable aromatic compound to alkylating agent of from about 0.5:1 to about 50:1, and a feed weight hourly space velocity (WHSV) based on the alkylating agent of from about 0.1 to 20 hr$^{-1}$.

16. The process of claim 1, wherein said alkylatable aromatic compound comprises benzene, said alkylating agent comprises propylene, said mono-alkylaromatic aromatic compound comprises cumene, said alkylation reaction conditions include a temperature of from about 10° C. to about 250° C., a pressure of from about 100 to about 3000 kPa-a, a molar ratio of alkylatable aromatic compound to alkylating agent of from about 0.5:1 to about 50:1, and a feed weight hourly space velocity (WHSV) based on the alkylating agent of from about 0.1 to 250 hr$^{-1}$.

17. The process of claim 1, wherein said alkylatable aromatic compound comprises benzene, said alkylating agent comprises butylene, said mono-alkylaromatic aromatic compound comprises sec-butylbenzene, said alkylation reaction conditions include a temperature of from about 10° C. to about 250° C., a pressure of from about 1 to about 3000 kPa-a, a molar ratio of alkylatable aromatic compound to alkylating agent of from about 0.5:1 to about 50:1, and a feed weight hourly space velocity (WHSV) based on the alkylating agent of from about 0.1 to 250 hr$^{-1}$.

18. A process for manufacturing a mono-alkylaromatic aromatic compound, said process comprising contacting a feedstock comprising an alkylatable aromatic compound and an alkylating agent under alkylation reaction conditions with a catalyst comprising EMM-13, said EMM-13 is a molecular sieve having, in its calcined form, an X-ray diffraction pattern including peaks at d-spacing maxima in the range of 14.17 to 12.57 Angstroms (~6.15-7.05 deg 2-θ), a d-spacing maximum in the range of 12.1 to 12.56 Angstroms (~7.3-7.05 deg 2-θ), a d-spacing maximum in the range of 10.14 to 12.0 Angstroms (8.7-7.35 deg 2-θ), and a d-spacing maximum in the range from 8.66 to 10.13 Angstroms (10.2-8.7 deg 2-θ); wherein said peaks having d-spacing maximum in the range of 10.14 to 12.0 Angstroms (8.7-7.35 deg 2-θ) and d-spacing maximum in the range from 8.66 to 10.13 Angstroms (10.2-8.7 deg 2-θ) exhibit a valley in between, wherein the measured intensity corrected for background at the lowest point of said valley is less than 50% of the intensity point at the same XRD d-spacing on the line connecting said peaks having d-spacing maxima in the range of 10.14 to 12.0 Angstroms (8.7-7.35 deg 2-θ) and in the range from 8.66 to 10.13 Angstroms (10.2-8.7 deg 2-θ); wherein said EMM-13 molecular sieve has less than 1.6 wt. % Ti.

* * * * *